(12) United States Patent
Shimada et al.

(10) Patent No.: US 10,864,371 B2
(45) Date of Patent: Dec. 15, 2020

(54) EXTERNAL STIMULATION OF THE CRANIAL NERVES

(71) Applicant: Nurelief, L.L.C., White Bear Lake, MN (US)

(72) Inventors: Jin Shimada, White Bear Lake, MN (US); Harry A. Puryear, Shoreview, MN (US)

(73) Assignee: Nurelief, L.L.C., White Bear Lake, MN (US)

( * ) Notice: Subject to any disclaimer, the term of this patent is extended or adjusted under 35 U.S.C. 154(b) by 143 days.

(21) Appl. No.: 16/180,119

(22) Filed: Nov. 5, 2018

(65) Prior Publication Data

US 2019/0134390 A1     May 9, 2019

Related U.S. Application Data

(60) Provisional application No. 62/581,733, filed on Nov. 5, 2017.

(51) Int. Cl.
| | |
|---|---|
| *A61N 1/36* | (2006.01) |
| *A61N 1/04* | (2006.01) |
| *A61N 2/02* | (2006.01) |

(52) U.S. Cl.
CPC ....... *A61N 1/36021* (2013.01); *A61N 1/0456* (2013.01); *A61N 1/36034* (2017.08); *A61N 1/0476* (2013.01); *A61N 1/0492* (2013.01); *A61N 1/36025* (2013.01)

(58) Field of Classification Search
USPC ...................................... 600/13; 607/45, 145
See application file for complete search history.

(56) References Cited

U.S. PATENT DOCUMENTS

| | | | |
|---|---|---|---|
| 2014/0081071 A1* | 3/2014 | Simon | A61N 1/36075 600/13 |
| 2015/0238762 A1* | 8/2015 | Pal | A61N 1/0492 607/45 |
| 2017/0197081 A1* | 7/2017 | Charlesworth | A61N 1/36025 |

* cited by examiner

*Primary Examiner* — Jon Eric C Morales

(57) ABSTRACT

Methods and devices for treating patients such as patients who suffer from migraine headaches including attaching electrodes of an electrical stimulation device to the patient bilaterally at a first location overlying a trigeminal nerve and at a second location overlying a second nerve, and then delivering electrical series of stimulation pulses to the patient, the stimulation pulses having a duration of between about 1 and about 20 microseconds, wherein the electrical stimulation device comprises a stimulation unit and a plurality of electrodes.

14 Claims, 4 Drawing Sheets

EXTERNAL STIMULATION OF THE CRANIAL NERVES

BACKGROUND

Disorders causing pain in the head and other neurological and mental health disorders cause sufferers significant pain and can impact their ability to work. For example, migraine sufferers experience recurrent, painful headaches which make it difficult for them to function. The mechanism of these disorders may be related to abnormal activity of the central nervous system and brain. Medical management of such disorders typically includes medications which, while often helpful, in many cases provide incomplete relief and may be accompanied by unwanted side effects.

For example, migraine headaches affect a large percent of people. Although the underlying causes of migraines are unknown, genetics and environmental stimulation are factors that influence susceptibility to migraine headaches. Migraine headaches may be a neurovascular disorder, with symptoms starting in the brain and spreading to the blood vessels. Theories include increased excitability of the cerebral cortex, abnormal control of pain neurons in the trigeminal nucleus of the brain stem, and increased levels of the neurotransmitter serotonin. Treatment with medication may reduce the symptoms and/or the rate of occurrence of migraine headaches. Other treatments include biofeedback and neuro stimulation with implanted stimulators. These treatments can help but are not ideal for many migraine sufferers and may provide incomplete relief.

Improved methods of treatment and prevention are therefore needed.

BRIEF DESCRIPTION OF THE DRAWINGS

The following drawings are illustrative of particular embodiments and do not limit the scope of the inventions. The drawings are not necessarily to scale and are intended for use in conjunction with the following detailed description. Embodiments of the inventions will be described with reference to the drawings, in which like numerals may represent like elements.

SUMMARY

Figure 1:
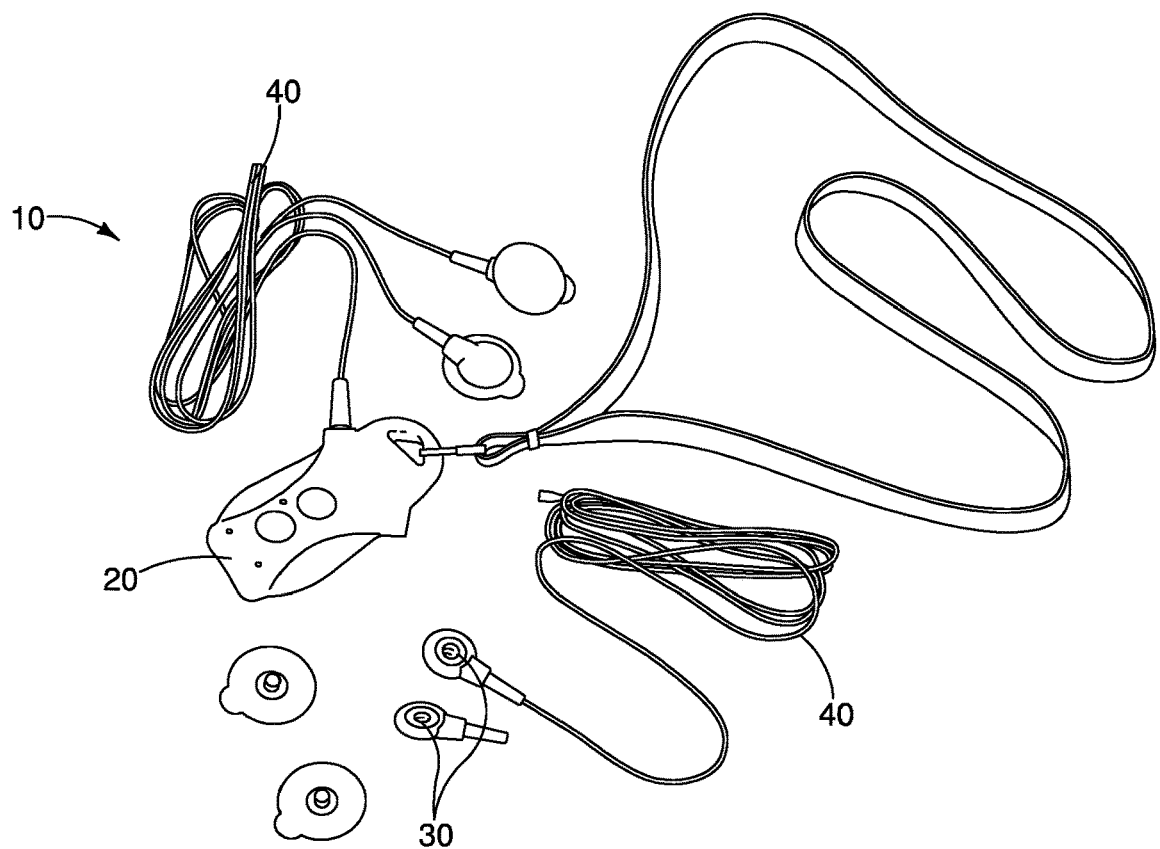
FIG. 1 is a photograph of a system for external stimulation according to various embodiments.

Various embodiments include method of treating a patient including attaching electrodes of an electrical stimulation device to a patient bilaterally at a first location overlying a trigeminal nerve and at a second location overlying a second nerve, and then delivering electrical series of stimulation pulses to the patient, the stimulation pulses having a duration of between about 1 and about 20 microseconds, wherein the electrical stimulation device comprises a stimulation unit and a plurality of electrodes. In some cases, the patient may be suffering from a headache at the time of treatment or the treatment is delivered prophylactically to reduce or prevent future headaches. The method may further adjusting an intensity of the electrical stimulation pulses as desired by the patient by increasing or decreasing the amplitude of the pulses. The stimulation pulses have a duration of between about 1 and about 10 microseconds and/or a frequency of between about 1 and about 200 Hz or between about 1 and about 100 Hz, for example.

In some embodiments, trigeminal nerve comprises a superficial branch of the trigeminal nerve such as the auriculotemporal nerve. In some such embodiments, the first location comprises may be the temple of the patient. The second nerve may also be a branch of the trigeminal nerve or a different cranial nerve or a peripheral nerve. In some embodiments, the second location may be a location on a face of a patient at a jaw line and directly anterior to and below an earlobe of the patient.

In some embodiments, the method of treating a patient suffering from a migraine headache includes, while the patient is suffering from a migraine headache, hanging an electrical stimulation unit from the patient's neck using a loop of flexible material attached to the electrical stimulation unit, attaching electrodes of an electrical stimulation device to the patient bilaterally at a first location overlying a portion of an auriculotemporal nerve and at a second location overlying a second nerve, and then delivering a series of electrical stimulation pulses to the patient at a frequency of between about 1 and about 1000 Hz and at a pulse duration of between about 1 and about 20 microseconds, wherein the electrical stimulation device comprises a stimulation unit and a plurality of electrodes. In some embodiments, the pulse duration may be about 1 to about 10 microseconds. The method may further include adjusting the electrical pulse duration and/or intensity during treatment. The first location may be a temple of the patient and the second location may be a location on a face or neck of the patient.

Other embodiments include an electrical simulation device system including an electrical stimulation unit comprising a power source, a pulse generator, a one or more unit controls, a first pair of electrodes connected to the electrical stimulation unit by a first lead, wherein the first lead bifurcates at an end at which the first pair of electrodes is located, a second pair of electrodes connected to the electrical stimulation unit by a second lead, wherein the second lead bifurcates at an end at which the second pair of electrodes is located, and a loop of flexible material, connected to the electrical stimulation unit and sized and configured to fit over a head of a user such that the electrical stimulation hangs on the users neck with the electrical stimulation unit approximately at the user's chest. The power source may be a rechargeable battery, and the system further include a charging cord and a case configured to enclose the electrical stimulation unit, leads, electrodes and charging cord. The controls may include controls to increase or decrease an intensity or duration of the electrical stimulation pulse therapy.

DETAILED DESCRIPTION

The following detailed description is exemplary in nature and is not intended to limit the scope, applicability, or configuration of the inventions. Rather, the following description provides practical illustrations for implementing various exemplary embodiments. Utilizing the teachings provided herein, those skilled in the art may recognize that many of the examples have suitable alternatives that may be utilized.

The devices and methods are related to those described in provisional patent application No. 62/339,330 and U.S. patent application Ser. No. 15/493,983, the disclosures of both of which are hereby incorporated by reference. In addition, the present application claims priority to U.S. Provisional application No. 62/581,733, the disclosure of which is hereby incorporated by reference.

Various embodiments provide prevention and/or treatment of pain in the head including headaches such as migraine headaches as well as psychological and neurological disorders through the use of stimulation of the superficial peripheral nerves by electrodes placed on and attached to the surface of the body directly over these nerves. Disorders which may be treated by the various embodiments include migraine headaches, depression, post-traumatic stress disorder (PTSD), and substance abuse and addition including narcotic use and addiction, among others. The devices described herein may be used while symptoms are present in order to reduce the symptoms and/or may be used while symptoms are not present in order to prevent or reduce the likelihood or severity of recurrence. For example, when used for the treatment of migraine headaches, the device may be used during a migraine headache in order to reduce the intensity of the pain. In addition, the device may be used when a patient is not experiencing a migraine in order to reduce the frequency and/or severity of future migraines. Likewise it may be used during bouts of depression, anxiety due to PTSD, or substance withdrawal, as well as during times when a patient is asymptomatic to prevent recurrence of such symptoms.

Figure 2:
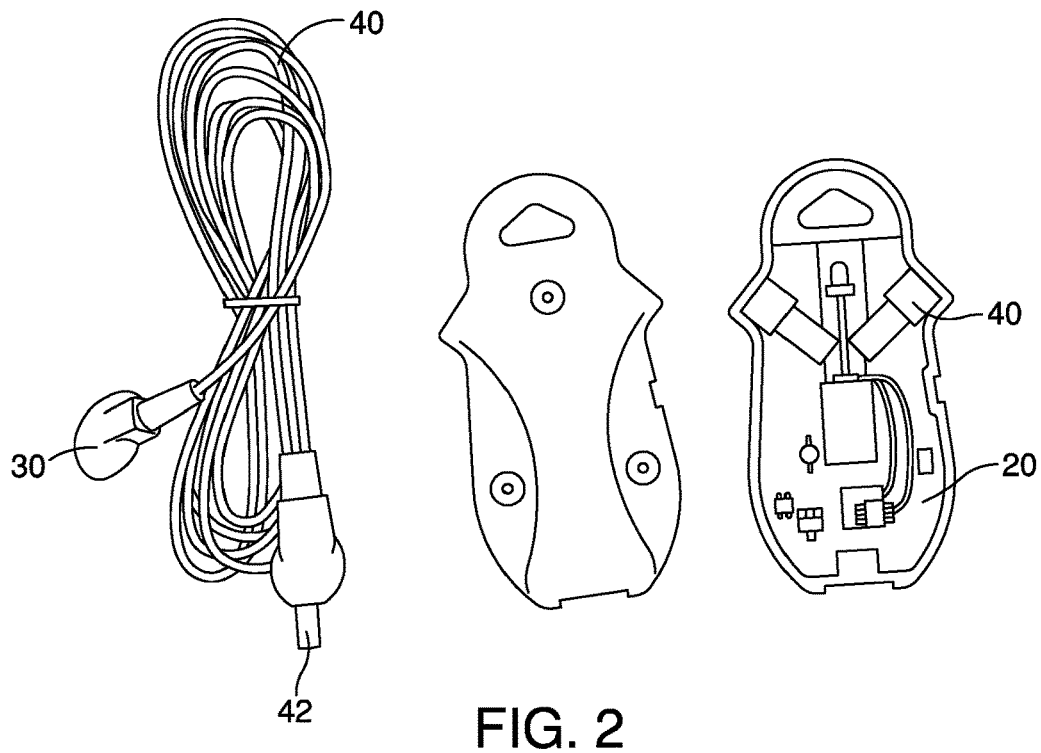
FIG. 2 is a photograph of the system of FIG. 1 with the housing of the stimulator open.
Figure 3:
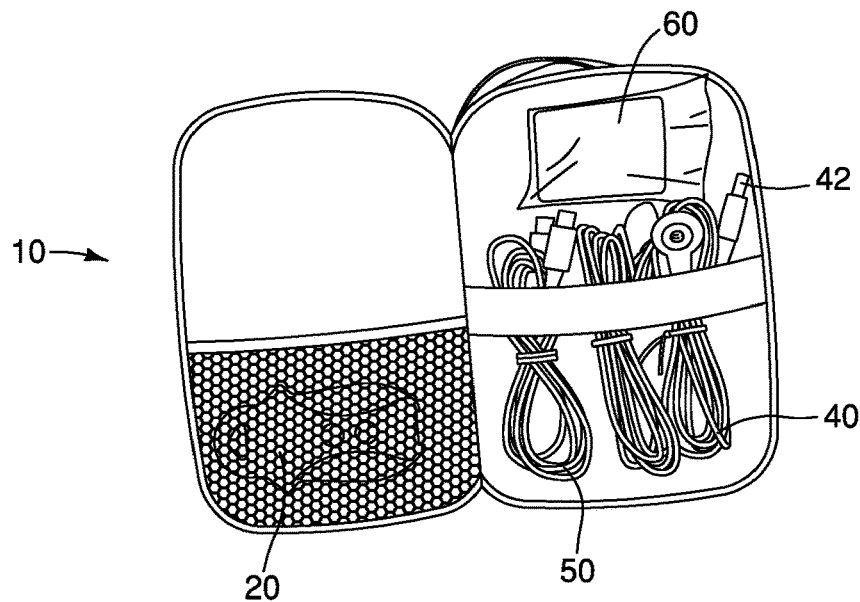
FIG. 3 is a photograph of the system of FIG. 1 stored within a case.

One embodiment of a stimulation system 10 for use in various embodiments is shown in FIGS. 1-3. The system 10 includes a stimulator 20 which provides the electrical stimulus and a set of external electrodes 30 on leads 40 which connect to the stimulator 20 and which attach to the user. In this embodiment, there are four electrodes 30, located in pairs on two leads 40, with each pair providing bipolar stimulation. The two leads include two connectors 42 for electrical connection with two connectors 22 in the stimulator 20.

As shown in FIG. 3, the system 10 may further include a charging cord 50 for recharging batteries within the stimulator 20. In the embodiment sown, the charging cord includes an electrical connector 54 for connecting to the stimulator 20 at electrical connector 24. The charging cord further includes an electrical connector 56 for connection to a power source. In this embodiment, the electrical connector 56 is a USB (Universal Serial Bus) connector, but in alternative embodiments the electrical connector 56 could be a two or three prong electrical plug or any other suitable connector for conducting power. In still other embodiments, the rechargeable batteries of the stimulator 20 may recharge outside of the stimulator 20 or by other methods or may use batteries that are not rechargeable. The system may further include a storage case 70 for storage and transportation.

Figure 4:
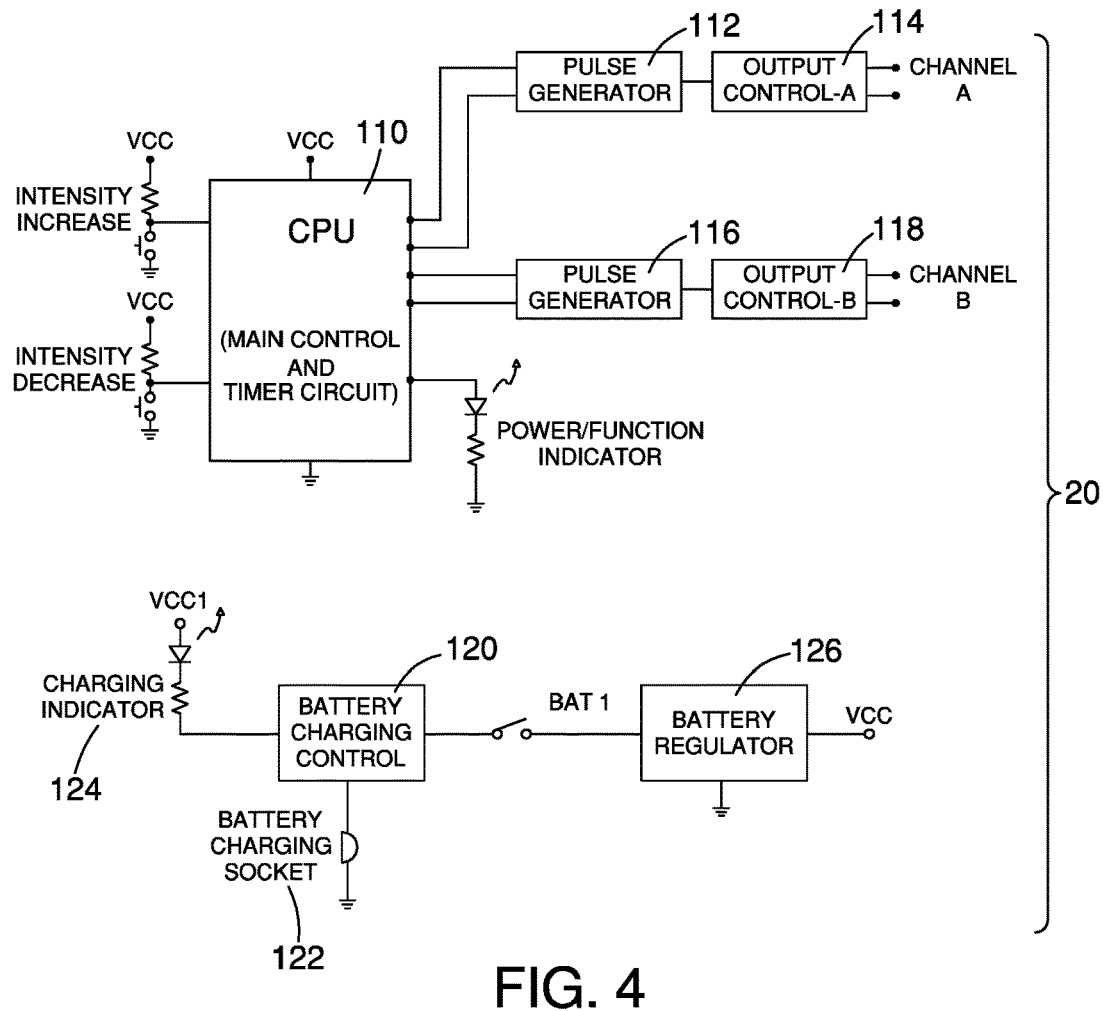
FIG. 4 is an image of a system for external stimulation according to various embodiments in use.

An example of an electrical diagram of the components and circuitry of a stimulator 20 is shown in FIG. 4. The stimulator 20 includes a central processing unit or CPU 110 which may include a main control and timer circuit for controlling the stimulation pulses. The CPU 110 is in electrical communication with a first pulse generator 112 and a first output control 114 as well as a second pulse generator 116 and a second output control 118. The CPU 110 is also in communication with resistors to increase or decrease the intensity of the stimulation pulse. The stimulator 20 also includes a battery charging control 120 in electrical communication with a battery charging socket 122 and a charging indicator 124. The battery charging control is also in electrical communication with a battery regulator 126 with a switch 128 there between. Power is supplied from through the battery regulatory to the CPU 110.

Figure 5:
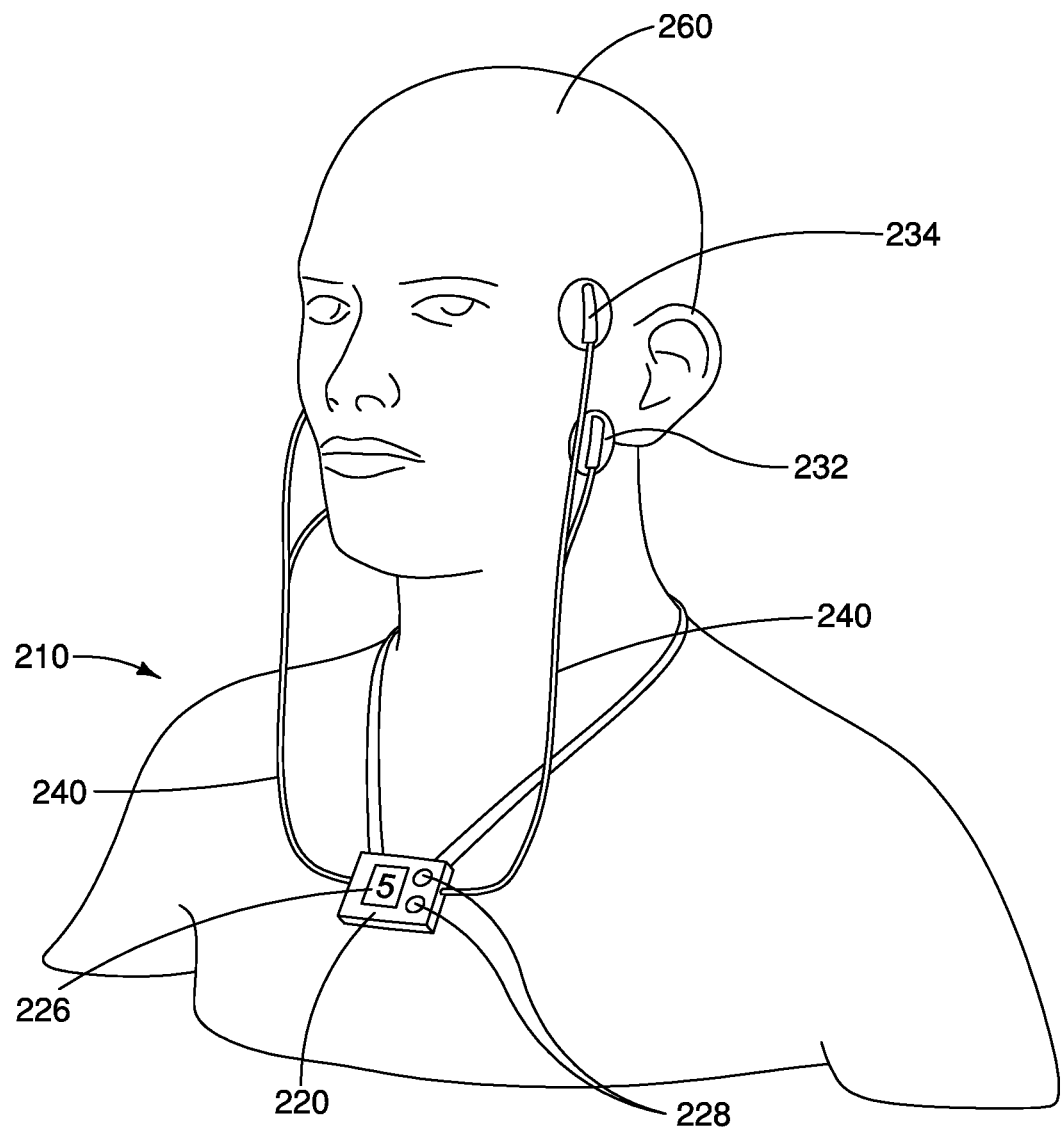
FIG. 5 is an electrical diagram of a stimulator according to various embodiments.

FIG. 5 shows an example of a system 210 in use. The stimulator 220 includes a pair of connectors 222 on each side of the stimulator 220 for connection to a lead 240 having a pair of electrodes 230 on each side of a head of a user 260. The stimulator 220 in this example includes a display screen 226 which may display the intensity level of the stimulation pulses, for example, as well as other information. The stimulator 210 also includes controls such as buttons 228 for a user to control the stimulator 220, such as to direct the stimulator 220 to increase or decrease the intensity of the stimulation pulses. The stimulator 220 also includes a pair of connectors 222 for electrical connection to leads 240.

In FIG. 5, each lead 240 connects to a pair of electrodes 230 including first electrode 232 and second electrode 242. The first electrode 232 is attached to the user 260 at the user's temple, approximately midway between the outer corner of the user's eye and the upper attachment point of the user's ear. The second electrode 242 is attached to the user along the face side of the user's jawline, in an approximately direct vertical line beneath the first electrode 232. These attachment points are chosen for delivery of electrical pulses to nerves which lie beneath these points, as described further below. As such, the precise location of these electrodes may vary somewhat provided that they overlie the desired nerves. A user may wear the stimulator 210 by hanging it from a loop of flexible material like a ribbon or cord around the user's neck as shown in FIG. 5, for example.

Embodiments described herein include methods of pain management and preventing, treating and/or reducing the symptoms of pain disorders of the head as well as mental disorders through the delivery of stimulation pulses to the superficial branches of the cranial nerves, in particular the trigeminal nerve (the fifth cranial nerve), as well as peripheral nerves. In some embodiments, electrical stimulation is delivered bilaterally to the auriculotemporal nerve, which is a superficial branch of the trigeminal nerve that extends from near the temporomandibular joint just in front of the ear upward toward the crown of the head. Electrodes placed at the temple as shown in FIG. 5 overlie the auriculotemporal nerve. The electrode at the jawline overlies peripheral nerves, and may optionally be placed elsewhere overlying peripheral nerves, such as elsewhere on the jaw, on the neck such as the back of the neck, or on the forehead. These positions are easy for a user to locate, making them good locations for electrode placement, although the electrodes could alternatively be placed at other locations along the superficial extent of the auriculotemporal nerve or other branches of the trigeminal nerve or other cranial nerves or peripheral nerves.

Figure 6:
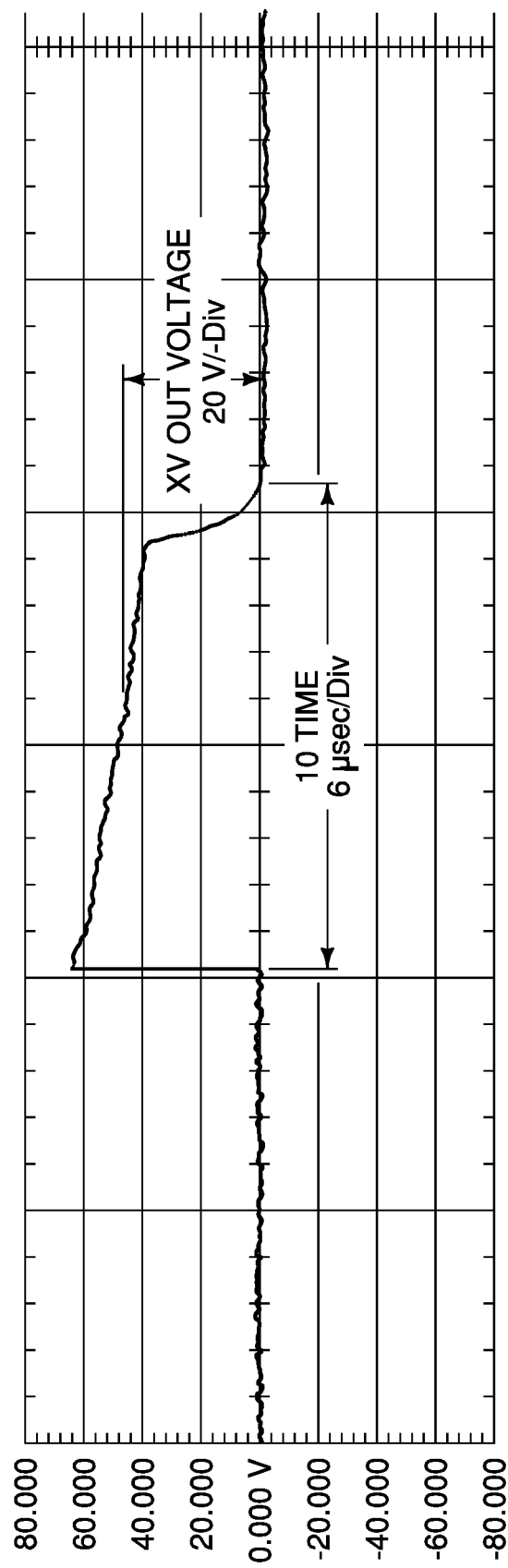
FIG. 6 is an example of a stimulation pulse according to various embodiments.

Various methods deliver a weak stimulation pulse to the superficial nerve branches of the trigeminal nerve such as the auriculotemporal nerve as well as other cranial nerves and/or peripheral nerves. The delivery of a direct current may modulate the activity and excitability of neurons which may enhance brain plasticity, the ability of the brain to recognize and transform itself. It may also reduce vascular resistance and increase vascular perfusion and flow rate. For example, the method may deliver pulses of a maximum of 2 milliamps to ensure user comfort, such as between about 0.5 and about 2 milliamps, or between about 1 milliamps and about 2 milliamps. The output voltage may be 0-120 Vpp, for example. The pulse frequency may be low, such as less than about 200 Hz or less than about 100 Hz. For example, the frequency may be between about 1 and about 200 Hz, or between about 1 and about 100 Hz. In some embodiments, the frequency may be between about 50 Hz and about 150 Hz, or between about 80 and about 120 Hz, or between about 80 and 100 Hz. In some embodiments, the frequency is about 100 Hz. In other embodiments, the frequency may be higher, such as between about 500 and 1500 Hz. The pulses may be short, such as less than about 200 microseconds, about 100 microseconds or less, or less than about 50 microseconds, or less than 20 microseconds, or less than 10 microseconds. For example, in various embodiments, the pulses may be between about 1 and about 200 microseconds, or between about 1 and about 100 microseconds, or between about 1 and about 50 microseconds, or between about 1 and about 20 microseconds, or between about 1 and 10 microseconds, or between about 1 and 5 microseconds in duration. The pulses may be delivered for a period of time between 1 minute and 1 hour, such as between about 15 minutes about 45 minutes or for about a half an hour. In some embodiments, the user may control the intensity, frequency and/or duration of the stimulation. An example of a stimulation pulse that may be used in various embodiments is shown in FIG. 6, in which the stimulation pulse width is 5 microseconds. The stimulation pulse may be delivered in a waveform such as a monophasic, modified square wave.

Experimental

In one experiment, external pulse stimulation as described herein was delivered to a group of 10 patients while experiencing a migraine headache attack. In each case, the electrodes of the stimulation device were attached to the individuals bilaterally at the temple and jawline as in the example shown in FIG. 5 and stimulation pulses were delivered for 30 minutes at 1000 Hz and 2.0 mA for a treatment time of 30 minutes, after which the device automatically shut off. Pain levels were rated by the individuals before, during and after stimulation treatment on a scale of 1-10, with 10 being the worst pain. In addition, in order to have an objective indication of pain relief, blood pressure was measured by the patients themselves using home-use upper arm blood pressure monitors before and after treatment, except in patients B, E, and H who were using blood pressure medication and therefore were not expected to have a normal blood pressure response to pain and pain relief. The results are shown in table 1 below.

TABLE 1

| Patient | Pain before | Pain during treatment | Pain after treatment | Systolic BP before | BP after | Change in systolic BP |
|---|---|---|---|---|---|---|
| | 9 | 6 within 10 mins. | 3 | 125 | 120 | −5 |
| | 10 | 5 within 10 mins. | 2 | — | — | — |
| | 8 | 5 within 5 mins. | 4 | 130 | 110 | −20 |
| | 8 | 3-4 within 5 mins. | 2 | 140 | 120 | −20 |
| | 9 | 5 within 10 mins. | 2 | — | — | — |
| | 8 | 4-5 within 10 mins. | 3 | 135 | 120 | −35 |
| | 9 | 5 within 10 mins. | 2 | 135 | 130 | −5 |
| | 10 | 5-6 within 10 mins. | 2 | — | — | — |
| | 7 | 5 within 10 mins. | 3 | 120 | 115 | −5 |
| | 9 | 5-6 within 10 mins. | 2 | 140 | 135 | −5 |

The results above show that a subjective assessment of pain was reduced within 5 to 10 minutes, and was dramatically reduced by the end of the 30 minute session. A blood pressure reduction also occurred, consistent with a decrease in the body's stress response to pain. On average, the patients rated their pain at 8.7 before the session, 4.5 within 10 minutes, and 2.5 after the treatment. Blood pressure reduced by an average of 9.375 mmHg.

In another experiment, external pulse stimulation as described herein was delivered to a group of 4 patients while experiencing a migraine headache attack. In each case, the electrodes of the stimulation device were attached to the individuals bilaterally at the temple and jawline as in the example shown in FIG. 5 and stimulation pulses were delivered for 30 minutes at a current of 0-130 mA, a pulse rate of 100 Hz and a pulse duration of 5 microseconds for a treatment time of 30 minutes, after which the device automatically shut off. Pain levels were rated by the individuals before, during and after stimulation treatment on a scale of 1-10, with 10 being the worst pain. In addition, in order to have an objective indication of pain relief, blood pressure was measured by the patients themselves using home-use upper arm blood pressure monitors before and after treatment. The results are shown in table 2 below.

TABLE 2

| Patient | Pain before | Pain at 10 minutes | Pain at 20 minutes | Pain after treatment | BP before | BP after | Change in BP |
|---|---|---|---|---|---|---|---|
| K | 3 | 3 | 2 | 1 | 128/90 | 122/84 | −6/−6 |
| L | 2 | 2 | 1 | 1 | 128/88 | 122/80 | −6/−8 |
| M | 3 | 2 | 2 | 1 | 126/88 | 120/80 | −6/−8 |
| N | 6 | 6 | 5 | 5 | 128/90 | 124/86 | −4/−6 |

The results above show that a subjective assessment of pain was reduced within 20 minutes, and was further reduced by the end of the 30 minute session. A blood pressure reduction also occurred, consistent with a decrease in the body's stress response to pain.

The invention claimed is:

1. A method of treating a patient comprising:
attaching electrodes of an electrical stimulation device to a patient bilaterally at a first location overlying a trigeminal nerve and at a second location overlying a second nerve, and then delivering electrical series of stimulation pulses to the patient, the stimulation pulses having a duration of between about 1 and about 10 microseconds,
wherein the electrical stimulation device comprises a stimulation unit and a plurality of electrodes.

2. The method of claim 1 wherein the patient is suffering from a headache at the time of treatment.

3. The method of claim 1 wherein the treatment is delivered prophylactically to reduce or prevent future headaches.

4. The method of claim 1 further comprising adjusting an intensity of the electrical stimulation pulses as desired by the patient by increasing or decreasing an amplitude of the electrical stimulation pulses.

5. The method of claim 1 wherein delivering electrical stimulation pulses comprises delivering electrical pulses at a frequency of between about 1 and about 200 Hz.

6. The method of claim 1 wherein delivering electrical stimulation pulses comprises delivering electrical pulses at a frequency of between about 1 and about 100 Hz.

7. The method of claim 1 wherein the trigeminal nerve comprises a superficial branch of the trigeminal nerve.

8. The method of claim 7 wherein the first superficial branch of the trigeminal nerve comprises an auriculotemporal nerve.

9. The method of claim 8 wherein the first location comprises a temple of the patient.

10. The method of claim 9 wherein the second nerve comprises a superficial peripheral nerve.

11. The method of claim 10 wherein the second location comprises a location on a face of a patient at a jaw line and directly anterior to and below an earlobe of the patient.

12. A method of treating a patient suffering from a migraine headache, the method comprising:
 while the patient is suffering from a migraine headache, hanging an electrical stimulation unit from the patient's neck using a loop of flexible material attached to the electrical stimulation unit;
 attaching electrodes of an electrical stimulation device to the patient bilaterally at a first location overlying a portion of an auriculotemporal nerve and at a second location overlying a second nerve, and then delivering a series of electrical stimulation pulses to the patient at a frequency of between about 1 and about 1000 Hz and at a pulse duration of between about 1 and about 10 microseconds, wherein the electrical stimulation device comprises a stimulation unit and a plurality of electrodes.

13. The method of claim 12 further comprising adjusting the electrical pulse duration and/or intensity during treatment.

14. The method of claim 12 wherein the first location comprises a temple of the patient and the second location comprises a location on a face or neck of the patient.

* * * * *